US009530058B2

(12) United States Patent
Moore et al.

(10) Patent No.: US 9,530,058 B2
(45) Date of Patent: Dec. 27, 2016

(54) VISUAL-ASSIST ROBOTS

(71) Applicant: Toyota Motor Engineering & Manufacturing North America, Inc., Erlanger, KY (US)

(72) Inventors: Douglas A. Moore, Livermore, CA (US); Joseph M. A. Djugash, San Jose, CA (US); Yasuhiro Ota, Santa Clara, CA (US); Shin Sano, San Francisco, CA (US); Sarah Rosenbach, Berkeley, CA (US); Sho Hiruta, San Francisco, CA (US); Maura Hoven, San Francisco, CA (US)

(73) Assignee: TOYOTA MOTOR ENGINEERING & MANUFACTURING NORTH AMERICA, INC., Erlanger, KY (US)

( * ) Notice: Subject to any disclaimer, the term of this patent is extended or adjusted under 35 U.S.C. 154(b) by 97 days.

(21) Appl. No.: 14/567,062

(22) Filed: Dec. 11, 2014

(65) Prior Publication Data

US 2016/0171303 A1 Jun. 16, 2016

(51) Int. Cl.
*G06K 9/00* (2006.01)
*G06K 9/78* (2006.01)
(Continued)

(52) U.S. Cl.
CPC .............. *G06K 9/00671* (2013.01); *A61F 9/08* (2013.01); *A61H 3/06* (2013.01); *B25J 5/00* (2013.01);
(Continued)

(58) Field of Classification Search
None
See application file for complete search history.

(56) References Cited

U.S. PATENT DOCUMENTS 6,083,353 A 7/2000 Alexander, Jr.
7,620,493 B2 11/2009 Stankiewicz et al.
(Continued)

FOREIGN PATENT DOCUMENTS

CN 102614068 A 8/2012
EP 1721237 8/2012
(Continued)

OTHER PUBLICATIONS

Search Report and Written Opinion pertaining to PCT/US15/60063 dated Jan. 21, 2016.
(Continued)

*Primary Examiner* — Stephen R Koziol
*Assistant Examiner* — Delomia L Gilliard
(74) *Attorney, Agent, or Firm* — Dinsmore & Shohl LLP (57) ABSTRACT

In one embodiment, a visual-assist robot includes a housing defining a base portion, an imaging assembly, a motorized wheel assembly positioned at the lower surface of the base portion, a processor disposed within the housing and communicatively coupled to the imaging assembly and the motorized wheel assembly, and a non-transitory memory device disposed within the housing. The imaging assembly generates image data corresponding to an environment, and at least a portion of the imaging assembly is configured to be disposed above the upper surface of the base portion. The non-transitory memory device stores machine-readable instructions that cause the processor to provide a drive signal to the motorized wheel assembly such that the motorized wheel assembly moves the visual-assist robot to a desired location within the environment, determine objects from the image data received from the imaging assembly, and transmit message data for receipt by a user.

20 Claims, 8 Drawing Sheets

(51) Int. Cl.
  *G06T 7/00* (2006.01)
  *A61H 3/06* (2006.01)
  *A61F 9/08* (2006.01)
  *B25J 5/00* (2006.01)
  *B25J 11/00* (2006.01)

(52) U.S. Cl.
  CPC .......... *B25J 11/008* (2013.01); *G06K 9/00201* (2013.01); *G06K 9/78* (2013.01); *G06T 7/004* (2013.01); *G06T 7/0051* (2013.01); *G06T 2207/10016* (2013.01); *G06T 2207/10028* (2013.01); *G06T 2207/20081* (2013.01)

(56) References Cited

U.S. PATENT DOCUMENTS

| | | | |
|---|---|---|---|
| 8,177,705 | B2 | 5/2012 | Abolfathi |
| 8,605,141 | B2 | 12/2013 | Dialameh et al. |
| 2007/0135962 | A1* | 6/2007 | Kawabe ................. G01S 17/74 700/225 |
| 2011/0172822 | A1* | 7/2011 | Ziegler .................. B25J 5/007 700/259 |
| 2011/0221670 | A1 | 9/2011 | King, III et al. |
| 2011/0232925 | A1* | 9/2011 | Al-Azemi .............. A62C 27/00 169/52 |
| 2012/0092161 | A1 | 4/2012 | West |
| 2013/0041292 | A1* | 2/2013 | Cunningham ......... A61B 18/12 601/2 |
| 2013/0093852 | A1 | 4/2013 | Ye |
| 2014/0100773 | A1 | 4/2014 | Cunningham et al. |
| 2014/0198442 | A1* | 7/2014 | Rekuc ................... A45C 13/26 361/679.09 |

FOREIGN PATENT DOCUMENTS

| | | | |
|---|---|---|---|
| JP | 2004033640 | A * | 2/2004 |
| JP | 20040033640 | A | 2/2004 |
| JP | 2007229854 | A * | 9/2007 |
| JP | 2009193240 | A * | 8/2009 |
| KR | 100857578 | B1 | 9/2008 |
| WO | 2008008791 | | 1/2008 |
| WO | 2010062481 | | 6/2010 |
| WO | 2014066690 | A2 | 5/2014 |

OTHER PUBLICATIONS

Japan develops robot that could take the place of seeing-eye dogs for visually-impaired people, Fareastgizmos, (http://fareastgizmos.com/robotic/japan-develops-robot-take-place-seeing-eye-dogs-visuallyirnpaired-people.php) (accessed Apr. 29, 2014).
OrCam—See for Yourself (http://www.orcam.com) (accessed Dec. 10, 2014).
GoPro Official Website: The World's Most Versatile Camera (http://gopro.com) (accessed Dec. 10, 2014).

* cited by examiner

VISUAL-ASSIST ROBOTS

TECHNICAL FIELD

The present specification generally relates to visual-assist devices and, more particularly, to visual-assist robots capable of providing users with information regarding objects within an environment.

BACKGROUND

Blind or visually impaired persons may find it difficult to navigate within their environment. Aid devices such as a cane may provide a visually impaired person with haptic feedback regarding objects that are within his or her vicinity. A guide dog may be used to assist in guiding a blind or visually impaired person through the environment. However, it may be very difficult for a blind or visually impaired person to have an understanding of objects within the environment, such as the location of people, obstacles, and signs.

Accordingly, a need exists for alternative devices for providing blind or visually impaired people with information regarding objects within an environment.

SUMMARY

In one embodiment, a visual-assist robot includes a housing defining a base portion having an upper surface and a lower surface, an imaging assembly, a motorized wheel assembly positioned at the lower surface of the base portion, a processor disposed within the housing and communicatively coupled to the imaging assembly and the motorized wheel assembly, and a non-transitory memory device disposed within the housing. The imaging assembly is configured to generate image data corresponding to an environment, and at least a portion of the imaging assembly is configured to be disposed above the upper surface of the base portion. The non-transitory memory device stores machine-readable instructions that, when executed by the processor, cause the processor to provide a drive signal to the motorized wheel assembly such that the motorized wheel assembly moves the visual-assist robot to a desired location within the environment, determine objects from the image data received from the imaging assembly, and transmit message data for receipt by a user. The message data provides an indication as to a presence of one or more objects determined from the image data.

In another embodiment, a visual-assist robot includes a housing defining a base portion having an upper surface and a lower surface, an imaging assembly, a retractable pedestal, a motorized wheel assembly positioned at the lower surface of the base portion, a wireless communication module configured to wirelessly communicate information with a portable electronic device, a processor disposed within the housing and communicatively coupled to the imaging assembly, the motorized wheel assembly, and the wireless communication module, and a non-transitory memory device disposed within the housing. The imaging assembly is configured to generate image data corresponding to an environment, and at least a portion of the imaging assembly is configured to be disposed above the upper surface of the base portion. The retractable pedestal is configured to extend from the upper surface of the base portion. The imaging assembly is coupled to the retractable pedestal such that when the retractable pedestal is in an extended position, the imaging assembly is disposed above the upper surface of the base portion, and when the retractable pedestal is in a retracted position, the imaging assembly is at least partially disposed within the base portion. The non-transitory memory device stores machine-readable instructions that, when executed by the processor, cause the processor to provide a drive signal to the motorized wheel assembly to autonomously move the visual-assist robot to a desired location within the environment, determine objects from the image data received from the imaging assembly and provide message data to the wireless communication module for wireless transmission to the portable electronic device. The message data provides an indication as to a presence of one or more objects determined from the image data These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 2:
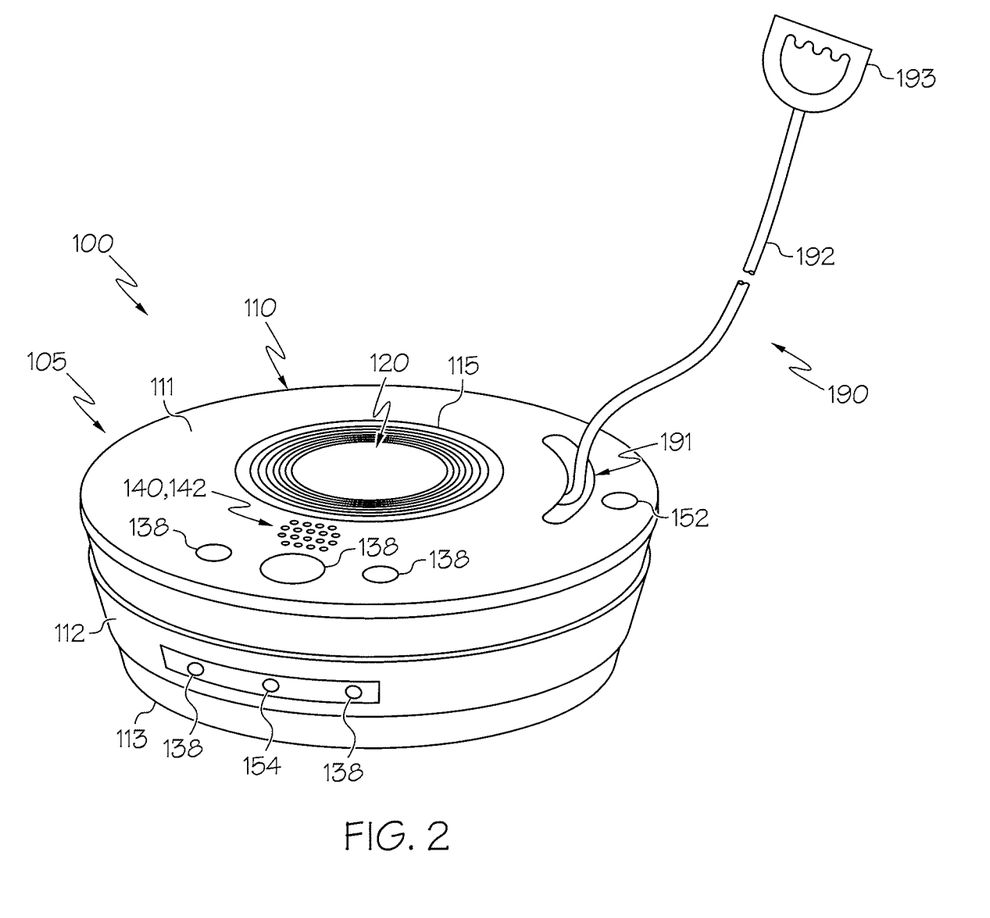
FIG. 2 schematically illustrates a top perspective view of a visual-assist robot with the retractable pedestal in a retracted position according to one or more embodiments described and illustrated herein.

Referring generally to FIG. 2, embodiments of the present disclosure are directed to visual-assist robots for use by blind or visually impaired users. The visual-assist robots described herein may provide users with an understanding of their surroundings. More specifically, the visual-assist robots described herein may autonomously navigate to a desired location, capture image data of the environment, and relay information to a user regarding objects in the environment in a manner that may be easily received by a blind or visually impaired individual. Various embodiments of visual-assist robots are described in detail below.

Figure 1:
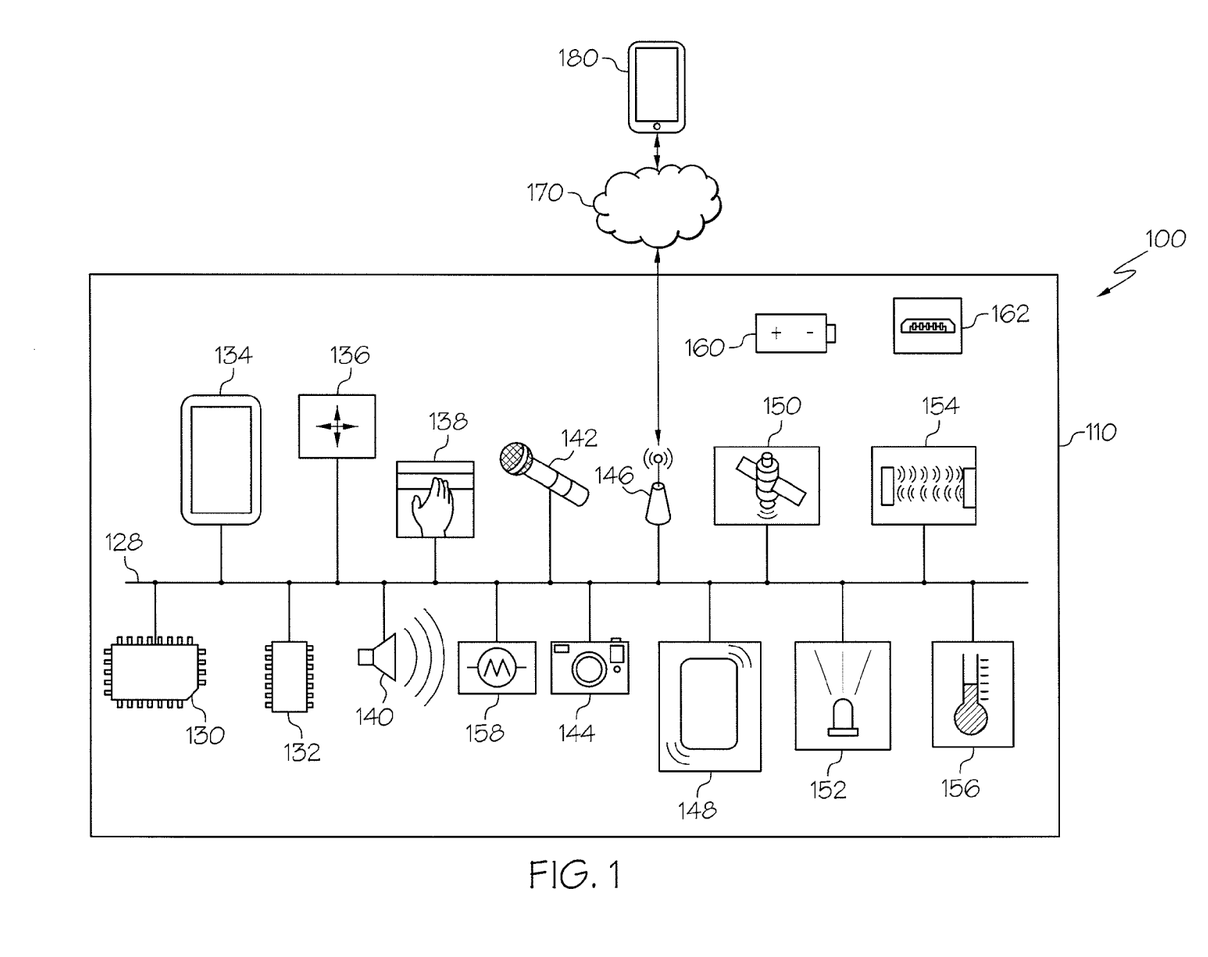
FIG. 1 schematically illustrates components of an example visual-assist robot according to one or more embodiments described and illustrated herein.

Referring now to FIG. 1, example components of one embodiment of a visual-assist robot 100 is schematically depicted. The visual-assist robot 100 includes a housing 110, a communication path 128, a processor 130, a memory module 132, a tactile display 134, an inertial measurement unit 136, an input device 138, an audio output device 140 (e.g., a speaker), a microphone 142, a camera 144, network interface hardware 146, a tactile feedback device 148, a location sensor 150, a light 152, a proximity sensor 154, a temperature sensor 156, a motorized wheel assembly 158, a battery 160, and a charging port 162. The components of the visual-assist robot 100 other than the housing 110 may be contained within or mounted to the housing 110. The various components of the visual-assist robot 100 and the interaction thereof will be described in detail below.

Still referring to FIG. 1, the communication path 128 may be formed from any medium that is capable of transmitting a signal such as, for example, conductive wires, conductive traces, optical waveguides, or the like. Moreover, the communication path 128 may be formed from a combination of mediums capable of transmitting signals. In one embodiment, the communication path 128 comprises a combination of conductive traces, conductive wires, connectors, and buses that cooperate to permit the transmission of electrical data signals to components such as processors, memories, sensors, input devices, output devices, and communication devices. Accordingly, the communication path 128 may comprise a bus. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The communication path 128 communicatively couples the various components of the visual-assist robot 100. As used herein, the term "communicatively coupled" means that coupled components are capable of exchanging data signals with one another such as, for example, electrical signals via conductive medium, electromagnetic signals via air, optical signals via optical waveguides, and the like.

The processor 130 of the visual-assist robot 100 may be any device capable of executing machine-readable instructions. Accordingly, the processor 130 may be a controller, an integrated circuit, a microchip, a computer, or any other computing device. The processor 130 is communicatively coupled to the other components of the visual-assist robot 100 by the communication path 128. Accordingly, the communication path 128 may communicatively couple any number of processors with one another, and allow the components coupled to the communication path 128 to operate in a distributed computing environment. Specifically, each of the components may operate as a node that may send and/or receive data. While the embodiment depicted in FIG. 1 includes a single processor 130, other embodiments may include more than one processor.

Still referring to FIG. 1, the memory module 132 of the visual-assist robot 100 is coupled to the communication path 128 and communicatively coupled to the processor 130. The memory module 132 may comprise RAM, ROM, flash memories, hard drives, or any non-transitory memory device capable of storing machine-readable instructions such that the machine-readable instructions can be accessed and executed by the processor 130. The machine-readable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine-readable instructions and stored in the memory module 132. Alternatively, the machine-readable instructions may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. While the embodiment depicted in FIG. 1 includes a single memory module 132, other embodiments may include more than one memory module.

The tactile display 134, if provided, is coupled to the communication path 128 and communicatively coupled to the processor 130. The tactile display 134 may be any device capable of providing tactile output in the form of refreshable tactile messages. A tactile message conveys information to a user by touch. For example, a tactile message may be in the form of a tactile writing system, such as Braille. A tactile message may also be in the form of any shape, such as the shape of an object detected in the environment. The tactile display 134 may provide information to the user regarding the operational state of the visual-assist robot 100.

Any known or yet-to-be-developed tactile display may be used. In some embodiments, the tactile display 134 is a three dimensional tactile display including a surface, portions of which may raise to communicate information. The raised portions may be actuated mechanically in some embodiments (e.g., mechanically raised and lowered pins). The tactile display 134 may also be fluidly actuated, or it may be configured as an electrovibration tactile display.

The inertial measurement unit 136, if provided, is coupled to the communication path 128 and communicatively coupled to the processor 130. The inertial measurement unit 136 may include one or more accelerometers and one or more gyroscopes. The inertial measurement unit 136 transforms sensed physical movement of the visual-assist robot 100 into a signal indicative of an orientation, a rotation, a velocity, or an acceleration of the visual-assist robot 100. The operation of the visual-assist robot 100 may depend on an orientation of the visual-assist robot 100 (e.g., whether the visual-assist robot 100 is horizontal, tilted, and the like). Some embodiments of the visual-assist robot 100 may not include the inertial measurement unit 136, such as embodiments that include an accelerometer but not a gyroscope, embodiments that include a gyroscope but not an accelerometer, or embodiments that include neither an accelerometer nor a gyroscope.

Still referring to FIG. 1, one or more input devices 138 are coupled to the communication path 128 and communicatively coupled to the processor 130. The input device 138 may be any device capable of transforming user contact into a data signal that can be transmitted over the communication path 128 such as, for example, a button, a switch, a knob, a microphone or the like. In some embodiments, the input device 138 includes a power button, a volume button, an activation button, a scroll button, or the like. The one or more input devices 138 may be provided so that the user may interact with the visual-assist robot 100, such as to navigate menus, make selections, set preferences, and other functionality described herein. In some embodiments, the input device 138 includes a pressure sensor, a touch-sensitive region, a pressure strip, or the like. It should be understood that some embodiments may not include the input device 138. As described in more detail below, embodiments of the visual-assist robot 100 may include multiple input devices disposed on any surface of the housing 110. In some embodiments, one or more of the input devices 138 are configured as a fingerprint sensor for unlocking the visual-assist robot. For example, only a user with a registered fingerprint may unlock and use the visual-assist robot 100.

The speaker 140 (i.e., an audio output device) is coupled to the communication path 128 and communicatively coupled to the processor 130. The speaker 140 transforms audio message data from the processor 130 of the visual-assist robot 100 into mechanical vibrations producing sound. For example, the speaker 140 may provide to the user navigational menu information, setting information, status information, information regarding the environment as detected by image data from the one or more cameras 144, and the like. However, it should be understood that, in other embodiments, the visual-assist robot 100 may not include the speaker 140.

The microphone 142 is coupled to the communication path 128 and communicatively coupled to the processor 130. The microphone 142 may be any device capable of transforming a mechanical vibration associated with sound into an electrical signal indicative of the sound. The microphone 142 may be used as an input device 138 to perform tasks, such as navigate menus, input settings and parameters, and any other tasks. It should be understood that some embodiments may not include the microphone 142.

Still referring to FIG. 1, the camera 144 is coupled to the communication path 128 and communicatively coupled to the processor 130. The camera 144 may be any device having an array of sensing devices (e.g., pixels) capable of detecting radiation in an ultraviolet wavelength band, a visible light wavelength band, or an infrared wavelength band. The camera 144 may have any resolution. The camera 144 may be an omni-directional camera, or a panoramic camera. In some embodiments, one or more optical components, such as a mirror, fish-eye lens, or any other type of lens may be optically coupled to the camera 144. As described in more detail below, the camera 144 is a component of an imaging assembly 122 operable to be raised above the housing 110 to capture image data.

The network interface hardware 146 is coupled to the communication path 128 and communicatively coupled to the processor 130. The network interface hardware 146 may be any device capable of transmitting and/or receiving data via a network 170. Accordingly, network interface hardware 146 can include a wireless communication module configured as a communication transceiver for sending and/or receiving any wired or wireless communication. For example, the network interface hardware 146 may include an antenna, a modem, LAN port, Wi-Fi card, WiMax card, mobile communications hardware, near-field communication hardware, satellite communication hardware and/or any wired or wireless hardware for communicating with other networks and/or devices. In one embodiment, network interface hardware 146 includes hardware configured to operate in accordance with the Bluetooth wireless communication protocol. In another embodiment, network interface hardware 146 may include a Bluetooth send/receive module for sending and receiving Bluetooth communications to/from a portable electronic device 180. The network interface hardware 146 may also include a radio frequency identification ("RFID") reader configured to interrogate and read RFID tags.

In some embodiments, the visual-assist robot 100 may be communicatively coupled to a portable electronic device 180 via the network 170. In some embodiments, the network 170 is a personal area network that utilizes Bluetooth technology to communicatively couple the visual-assist robot 100 and the portable electronic device 180. In other embodiments, the network 170 may include one or more computer networks (e.g., a personal area network, a local area network, or a wide area network), cellular networks, satellite networks and/or a global positioning system and combinations thereof. Accordingly, the visual-assist robot 100 can be communicatively coupled to the network 170 via wires, via a wide area network, via a local area network, via a personal area network, via a cellular network, via a satellite network, or the like. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, and/or other near field communication protocols. Suitable personal area networks may similarly include wired computer buses such as, for example, USB and FireWire. Suitable cellular networks include, but are not limited to, technologies such as LTE, WiMAX, UMTS, CDMA, and GSM.

Still referring to FIG. 1, as stated above, the network 170 may be utilized to communicatively couple the visual-assist robot 100 with the portable electronic device 180. The portable electronic device 180 may include a mobile phone, a smartphone, a personal digital assistant, a camera, a dedicated mobile media player, a mobile personal computer, a laptop computer, and/or any other portable electronic device capable of being communicatively coupled with the visual-assist robot 100. The portable electronic device 180 may include one or more processors and one or more memories. The one or more processors can execute logic to communicate with the visual-assist robot 100. The portable electronic device 180 may be configured with wired and/or wireless communication functionality for communicating with the visual-assist robot 100. In some embodiments, the portable electronic device 180 may perform one or more elements of the functionality described herein, such as in embodiments in which the functionality described herein is distributed between the visual-assist robot 100 and the portable electronic device 180.

The tactile feedback device 148 is coupled to the communication path 128 and communicatively coupled to the processor 130. The tactile feedback device 148 may be any device capable of providing tactile feedback to a user. The tactile feedback device 148 may include a vibration device (such as in embodiments in which tactile feedback is delivered through vibration), an air blowing device (such as in embodiments in which tactile feedback is delivered through a puff of air), or a pressure generating device (such as in embodiments in which the tactile feedback is delivered through generated pressure). It should be understood that some embodiments may not include the tactile feedback device 148.

The location sensor 150 is coupled to the communication path 128 and communicatively coupled to the processor 130. The location sensor 150 may be any device capable of generating an output indicative of a location. In some embodiments, the location sensor 150 includes a global positioning system (GPS) sensor, though embodiments are not limited thereto. Some embodiments may not include the location sensor 150, such as embodiments in which the visual-assist robot 100 does not determine a location of the visual-assist robot 100 or embodiments in which the location is determined in other ways (e.g., based on information received from the camera 144, the microphone 142, the network interface hardware 146, the proximity sensor 154, the inertial measurement unit 136 or the like). The location sensor 150 may also be configured as a wireless signal sensor capable of triangulating a location of the visual-assist robot 100 and the user by way of wireless signals received from one or more wireless signal antennas.

The motorized wheel assembly 158 is coupled to the communication path 128 and communicatively coupled to the processor 130. As described in more detail below, the motorized wheel assembly 158 includes motorized wheels 195A, 195B (see FIG. 5) that are driven by one or motors (not shown). The processor 130 may provide one or more drive signals to the motorized wheel assembly 158 to actuate the motorized wheels 195A, 195B such that the visual-assist robot 100 travels to a desired location, such as a location that the user wishes to acquire environmental information (e.g., the location of particular objects within at or near the desired location).

Still referring to FIG. 1, the light 152 is coupled to the communication path 128 and communicatively coupled to the processor 130. The light 152 may be any device capable of outputting light, such as, but not limited to, a light emitting diode, an incandescent light, a fluorescent light, or the like. Some embodiments include a power indicator light that is illuminated when the visual-assist robot 100 is powered on. Some embodiments include an activity indicator light that is illuminated when the visual-assist robot 100 is active or processing data. Some embodiments include an illumination light for illuminating the environment in which the visual-assist robot 100 is located. Some embodiments may not include the light 152.

The proximity sensor 154 is coupled to the communication path 128 and communicatively coupled to the processor 130. The proximity sensor 154 may be any device capable of outputting a proximity signal indicative of a proximity of the visual-assist robot 100 to another object. In some embodiments, the proximity sensor 154 may include a laser scanner, a capacitive displacement sensor, a Doppler effect sensor, an eddy-current sensor, an ultrasonic sensor, a magnetic sensor, an optical sensor, a radar sensor, a sonar sensor, or the like. Some embodiments may not include the proximity sensor 154, such as embodiments in which the proximity of the visual-assist robot 100 to an object is determine from inputs provided by other sensors (e.g., the camera 144, the speaker 140, etc.) or embodiments that do not determine a proximity of the visual-assist robot 100 to an object.

The temperature sensor 156 is coupled to the communication path 128 and communicatively coupled to the processor 130. The temperature sensor 156 may be any device capable of outputting a temperature signal indicative of a temperature sensed by the temperature sensor 156. In some embodiments, the temperature sensor 156 may include a thermocouple, a resistive temperature device, an infrared sensor, a bimetallic device, a change of state sensor, a thermometer, a silicon diode sensor, or the like. Some embodiments of the visual-assist robot 100 may not include the temperature sensor 156.

Still referring to FIG. 1, the visual-assist robot 100 is powered by the battery 160, which is electrically coupled to the various electrical components of the visual-assist robot 100. The battery 160 may be any device capable of storing electric energy for later use by the visual-assist robot 100. In some embodiments, the battery 160 is a rechargeable battery, such as a lithium-ion battery or a nickel-cadmium battery. In embodiments in which the battery 160 is a rechargeable battery, the visual-assist robot 100 may include the charging port 162, which may be used to charge the battery 160. Some embodiments may not include the battery 160, such as embodiments in which the visual-assist robot 100 is powered the electrical grid, by solar energy, or by energy harvested from the environment. Some embodiments may not include the charging port 162, such as embodiments in which the apparatus utilizes disposable batteries for power.

Figure 3:
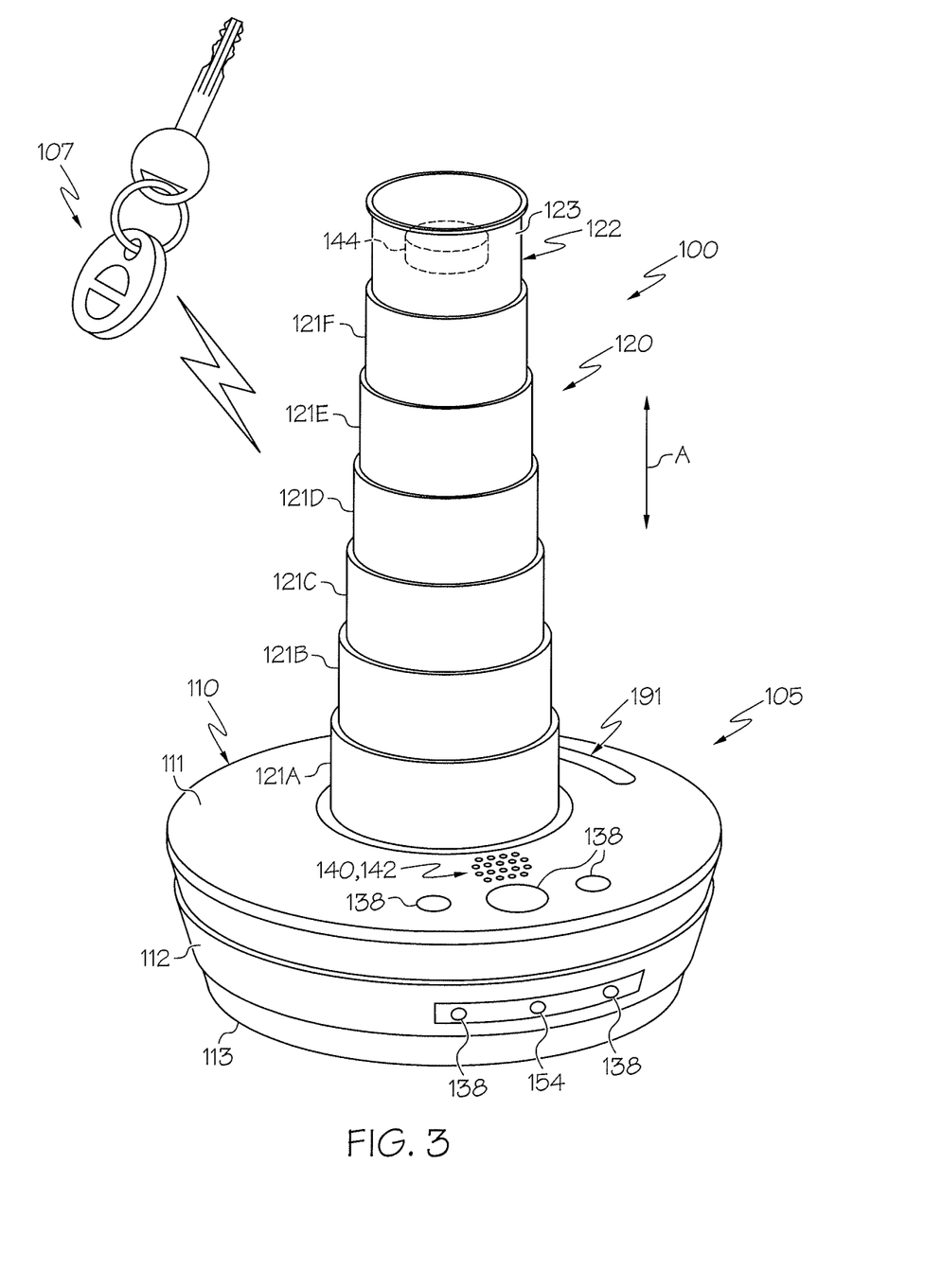
FIG. 3 schematically illustrates a top perspective view of a visual-assist robot with the retractable pedestal in an extended position according to one or more embodiments described and illustrated herein.

Referring now to FIGS. 2 and 3, an example visual-assist robot 100 is schematically illustrated. The visual-assist robot 100 is of a size and weight that is small enough for users to pick up and carry with them. For example, the visual-assist robot 100 may fit in a purse or bag such that the user may carry the visual-assist robot 100 until it is needed.

Generally, the example visual-assist robot 100 includes a housing 110 defining a base portion 105, a retractable pedestal 120 coupled to the base portion 105, and an imaging assembly 122 coupled to the retractable pedestal 120. It is noted that FIG. 2 depicts the retractable pedestal 120 in a retracted position such that the retractable pedestal 120 and the imaging assembly 122 are disposed within the base portion 105, while FIG. 3 depicts the retractable pedestal 120 in an extended position such that the imaging assembly 122 is positioned above the base portion 105. When retractable pedestal 120 is in the extended position, the imaging assembly 122 is in a higher position to capture images of the surrounding area. Exemplary aspects and features of the imaging assembly 122 are described in more detail below.

Still referring to both FIGS. 2 and 3, the housing 110 defines an upper surface 111 and a lower surface 113 separated by a perimeter surface 112. The components described above with respect to FIG. 1 may be disposed within or on the housing 110. It should be understood that the arrangement of the components depicted in FIGS. 2 and 3 is for illustrative purposes only, and that embodiments are not limited thereto. In the illustrated embodiment, the upper surface 111 of the housing 110 has an opening 115 from which the retractable pedestal 120 extends.

Several input devices 138 are also provided at the upper surface 111 of the housing 110. As shown in FIGS. 2 and 3, one or more input devices 138 may also be provided at the perimeter surface 112. As stated above, the input devices 138 may take on many forms, such as mechanical buttons and touch-sensitive regions (e.g., by capacitive or resistive touch layers). Any number of input devices 138 may be provided at the upper surface 111. In other embodiments, no input devices 138 are provided at the upper surface 111. In one embodiment, at least one of the input devices 138 is configured as a fingerprint sensor. The user may place his or her finger on the fingerprint sensor. The fingerprint sensor may send a signal representing the user's fingerprint to the processor 130, which then detects the user's fingerprint. The visual-assist robot 100 may be unlocked for operation by the user if the detected fingerprint matches data representing the user's fingerprint that is stored in the memory module 132. The input devices 138 may also be used for other functionality, such as to turn the visual-assist robot on and off, to navigate menus (e.g., auditory menus), to input settings and parameters into the visual-assist robot 100, and to extend or retract the retractable pedestal 120 in embodiments wherein the retractable pedestal 120 is mechanically actuated, as described in more detail below.

Also disposed within the upper surface 111 of example base portion 105 are openings for a speaker 140 and a microphone 142 that may be disposed within the base portion 105. The speaker 140 may receive message data from the processor 130 and generate an audio message in the form of sound in accordance with the information provided by the message data. For example, the message data may correspond to topographic information with respect to the environment, audio hierarchical menus, or requests for the user to provide input to the visual-assist robot 100. The microphone 142 may be provided for the user to provide inputs to the visual-assist robot 100 using his or her voice. It should be understood that the speaker 140 and microphone 142 may be proximate a surface of the base portion 105 other than the upper surface 111, such as the perimeter surface 112, for example.

In the illustrated embodiment, a light 152 is provided on the upper surface 111 of the base portion 105. The light 152 may be illuminated while the visual-assist robot 100 is operating to alert people in the environment as to its presence. In some embodiments, the light 152 may be configured as a pulsing or continuously-on light emitting diode. It should be understood that the light 152 may be positioned on the visual-assist robot 100 in a location other than that depicted in FIGS. 2 and 3, and that in some embodiments, no light 152 may be provided.

The example visual-assist robot 100 further includes a retractable handle assembly 190 comprising a handle 193 and a retractable cord 192. In the illustrated embodiment, the upper surface 111 of the housing 110 includes a storage recess 191 having an opening that corresponds with the shape and size of the handle 193 such that the handle 193 and retractable cord 192 are disposed within the storage recess 191 when retractable handle assembly 190 is in a retracted position. The user may grasp and pull the handle 193 such that the retractable cord 192 uncoils within the base portion 105 as shown in FIG. 2. The user may use the retractable handle assembly 190 to pull the visual-assist robot 100 to a desired location. The retractable cord 192 may automatically coil within the base portion 105 when the user moves the handle 193 toward the storage recess 191. Any mechanism capable of automatically coiling and uncoiling the retractable cord 192 may be provided within the base portion 105. It should be understood that other configurations for the retractable handle assembly 190 are also possible and, in some embodiments, no retractable handle assembly 190 is provided.

The example visual-assist robot 100 includes a proximity sensor 154 in the perimeter surface 112 of the base portion 105. Any number of proximity sensors 154 may be provided in the perimeter surface 112 (or any surface). As described above with respect to FIG. 1, the proximity sensor 154 generates one or more signals based on the presence of one or more objects. The proximity sensor(s) 154 may be used by the visual-assist robot 100 to detect and avoid obstacles (e.g., people, furniture, stairs, walls, and the like) as it autonomously navigates within the environment while capturing image data for relaying to the user in a manner that does not rely on human vision.

Referring specifically to FIG. 3, the retractable pedestal 120 is shown in an expanded position such that the imaging assembly 122 is disposed above the upper surface 111 of the base portion 105. By moving the imaging assembly 122 above the base portion 105, the imaging assembly 122 may have a better view of the environment to capture image data. In the illustrated embodiment, the retractable pedestal 120 comprises segments 121A-121F. The segments 121A-121F are positioned in a nested arrangement and stored within the base portion 105 when the retractable pedestal 120 is in a retracted position as shown in FIG. 2. When in an expanded position, the segments form a retractable pedestal 120 on which the imaging assembly 122 is positioned. Any number of segments may be provided. In the illustrated embodiment, the imaging assembly is coupled to segment 121F. It should be understood that the retractable pedestal 120 is not limited to use of segments, and that any structure capable of raising and lowering the imaging assembly may be utilized.

In some embodiments, the retractable pedestal 120 may be mechanically actuated based on an input received from one or more input device 138. The visual-assist robot 100 may include, within the base portion 105, any mechanism (not shown) capable of raising and lowering the imaging (not shown) assembly 122 in a direction indicated by arrow A by expanding and retracting the retractable pedestal 120. In other embodiments, the retractable pedestal 120 may not be mechanically actuated. Rather, the user may pull the imaging assembly 122 up when image data capture is desired, and push the imaging assembly 122 back into the base portion 105 when image data capture is not desired. Features (not shown) may be provided on the imaging assembly 122 and/or base portion 105 to enable the user to release the imaging assembly 122 from the base portion 105 and pull it up so that the retractable pedestal 120 is in the expanded position.

The imaging assembly 122 is configured to capture image data of the environment within the vicinity of the visual-assist robot 100. In some embodiments, the imaging assembly 122 includes a camera 144 that is surrounded by an imaging assembly housing 123. The imaging assembly housing 123 may be made of a material that is substantially transparent to the wavelength of the radiation detected by the camera 144 (e.g., wavelengths within the visual spectrum). In some embodiments, the camera 144 is configured to capture omni-directional image data. For example, the camera 144 may rotate about an axis to capture image data about three-hundred and sixty degrees surrounding the visual-assist robot 100. Further, the camera 144 may be configured to automatically tilt up and down to capture additional image data that would otherwise be out of view if the camera 144 did not tilt up and down.

In some embodiments, the imaging assembly 122 is removably coupled to the retractable pedestal 120 so that the user may lift the imaging assembly 122 to a position higher than that provided by the retractable pedestal 120. The imaging assembly 122 may include its own wireless communication hardware (e.g., Bluetooth hardware) to communicate with the components within the base portion 105. In this manner, image data may be captured by the removed imaging assembly 122 and wirelessly communicated to the processor 130 within the base portion 105.

Figure 4:
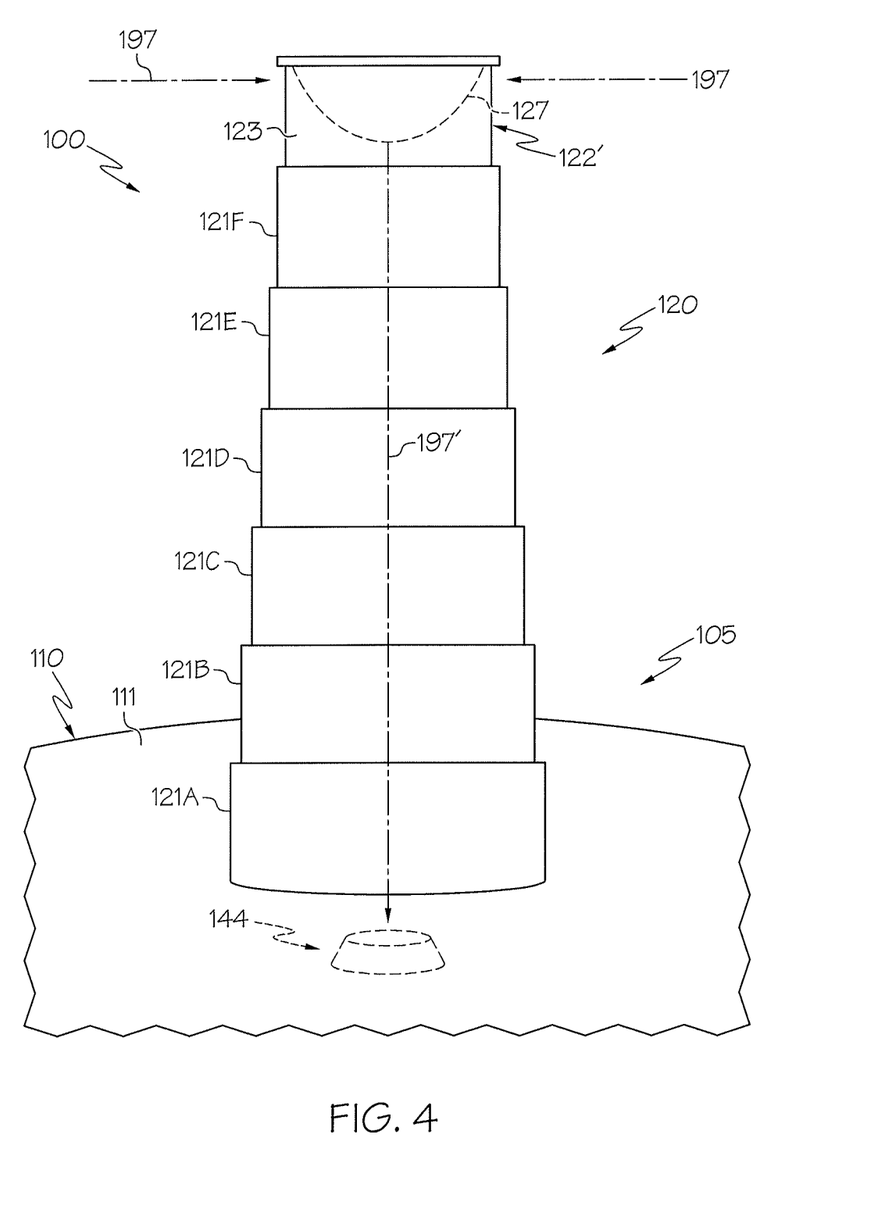
FIG. 4 schematically illustrates the retractable pedestal in an extended position and an imaging assembly having an omni-directional mirror according to one or more embodiments described and illustrated herein.

Referring now to FIG. 4, an example configuration of an imaging assembly 122' is schematically illustrated. In the illustrated embodiment, the camera 144 is disposed within the base portion 105, and an omni-directional mirror 127 is disposed within the imaging assembly housing 123. Light 197 is incident on the omni-directional mirror 127 from all directions (i.e., three-hundred and sixty degrees) and is reflected by the omni-directional mirror 127 as reflected light 197'. An interior region of the retractable pedestal 120 provides an optical path for the reflected light 197', which is received by the camera 144. The camera 144 produces omni-directional image data, which is provided to the processor 130 for analysis. Additional optical components, such as lenses (not shown) may be provided in the optical path of the reflected light 197' to condition it for receipt by the camera 144.

Referring once again to FIG. 3, the visual-assist robot 100 may be configured to communicate with a remote control device 107. The example remote control device 107 depicted in FIG. 3 is illustrated as a key fob, but embodiments are not limited thereto. The visual-assist robot 100 may wirelessly communicate with the remote control device 107 using the network interface hardware 146, for example. The remote control device 107 may provide several functionalities. For example, the remote control device 107 may be used provide inputs (e.g., commands, settings, and parameters) to the visual-assist robot 100, to remotely maneuver the visual-assist robot 100 to the desired location, and provide user proximity information to the visual-assist robot 100. For example, in some embodiments, the visual-assist robot 100 may cease operating when it is more than a threshold distance from the remote control device 107. The visual-assist robot 100 may produce an audio alarm (e.g., a siren) and/or visual alarm (e.g., a strobing light 152) when the visual-assist robot 100 is more than a threshold distance from the remote control device 107.

Figure 5:
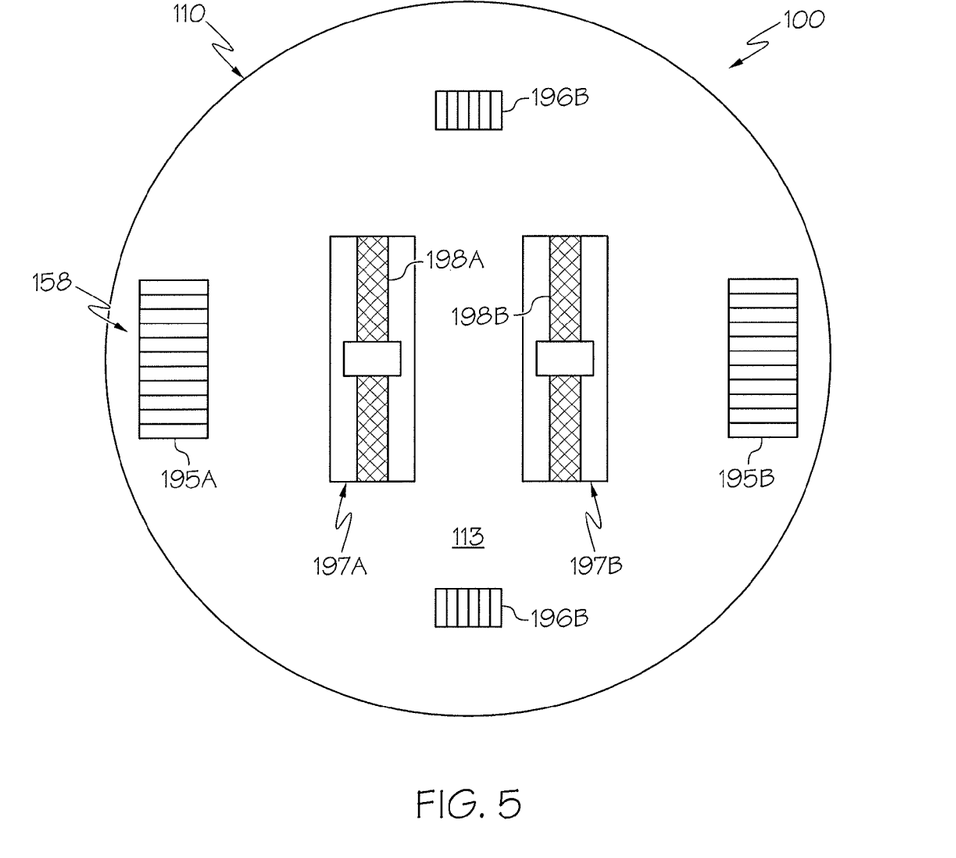
FIG. 5 schematically illustrates a lower surface of a visual-assist robot according to one or more embodiments described and illustrated herein.

Referring now to FIG. 5, a lower surface 113 of the base portion 105 of the visual-assist robot 100 is schematically depicted. In the illustrated embodiment, two motorized wheels 195A, 195B define the motorized wheel assembly 158 schematically depicted in FIG. 1. The motorized wheels 195A, 195B may turn in any direction to provide omni-directional movement for the visual-assist robot 100. Any type of motor or motors may be used to drive the motorized wheels 195A, 195B. The motorized wheel assembly 158 receives one or more drive signals from the processor 130 that control the motorized wheels 195A, 195E to move the visual-assist robot 100 to the desired location. The motorized wheel assembly 158 may take on other configurations, and may include more or fewer than two motorized wheels 195A, 195B. In the illustrated embodiment, two auxiliary wheels 196A, 196B are also provided to balance the visual-assist robot 100.

Two retractable carrying straps 198A, 198B are also provided at the lower surface 113 of the base portion 105 in the illustrated embodiment. The retractable carrying straps 198A, 198B are configured to be placed on the user's body, such as around his or her shoulders so that the user may carry the visual-assist robot 100 like a backpack when transporting the visual-assist robot 100. Carrying straps may be provided at a location(s) other than the lower surface 113 in other embodiments. More or fewer carrying straps may be provided. Alternatively, no carrying straps may be provided.

As stated above, the visual-assist robot 100 may be used by blind or visually impaired users to gain an understanding of their environment. More particularly, the visual-assist robot 100 captures image data of the surrounding environment, extracts relevant information about the environment, and presents that information to the user in a non-visual manner. The visual-assist robot 100 may autonomously navigate to a desired location at the command of the user, capture desired information regarding the surrounding environment, and then provide the information to the user.

Figure 6:
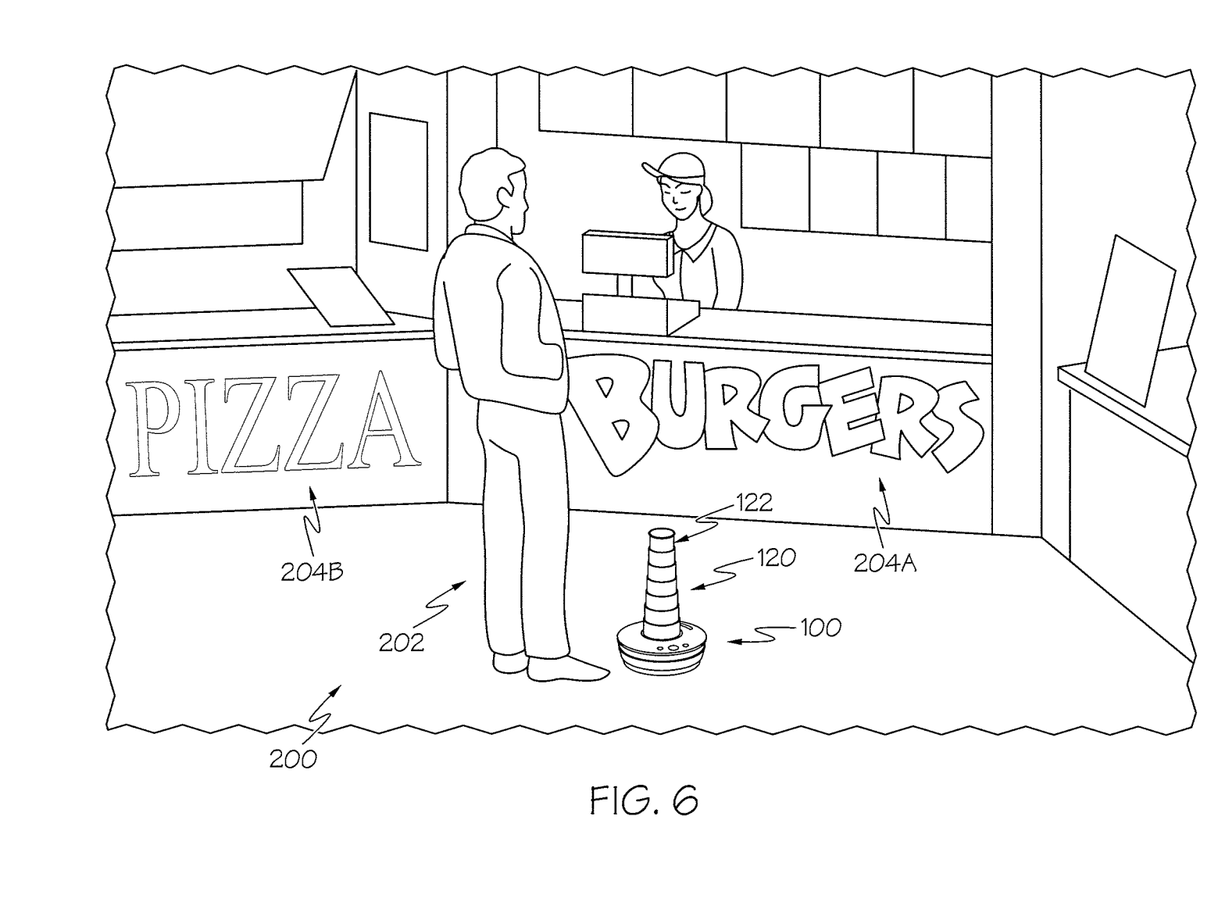
FIGS. 6-8 schematically illustrate a user operating an example visual-assist robot in an environment according to one or more embodiments described and illustrated herein.

An example use-case of the visual-assist robot 100 will now be described with reference to FIGS. 6-8. It should be understood that embodiments are not limited to the example use-case described below. Referring to FIG. 6, a blind or visually impaired user 202 of a visual-assist robot 100 may be in an environment 200 where he or she needs visual assistance. In the illustrated example, a user 202 is in a food court. The user 202 may wish to purchase food but does not know where the individual restaurants are located and also does not know the names of the individual restaurants or what types of food the individual restaurants sell.

Using the input devices 138 and/or the microphone 142, the user may provide a command to the visual-assist robot 100 to autonomously navigate to a desired location which may be in the middle of the food court or some area. In some embodiments, speech recognition machine-readable instructions are stored in the memory module 132 and are executed by the processor 130. The speech recognition instructions may enable the processor 130 to recognize audio instructions spoken by the user. For example, the user 202 may speak "go to the center of the room" into the visual-assist robot 100, a portable electronic device 180 (e.g., a cellular telephone), or a remote control device 107 (e.g., a key fob). The processor 130 may then extract the command from the spoken words and provide a drive signal to the motorized wheel assembly 158 to cause the visual-assist robot 100 to navigate to the desired location. Alternatively, the user may only use the input device 138 on visual-assist robot 100 and/or input devices on the portable electronic device 180 or the remote control device 107.

When navigating the environment, the retractable pedestal 120 is in an expanded position such that the imaging assembly 122 is raised above the base portion. Machine-readable instructions stored in the memory module 132 executed by the processor 130 cause the visual-assist robot 100 to create a navigation route and navigate the navigation route while avoiding obstacles. Any known or yet-to-be developed autonomous navigation techniques may be used to control the visual-assist robot 100 to autonomously navigate to the desired location (i.e., the location indicated by the user).

The navigation route may be determined by any combination of the captured image data from the imaging assembly 122, the location sensor 150, the proximity sensor 154, and the network interface hardware 146. The image data captured by the imaging assembly 122 may be a single image or a plurality of sequential images. The image data captured by the imaging assembly 122 may be provided to the processor 130, which then analyzes the image data. One or more object recognition algorithms may be applied to the image data to extract particular objects. Any known or yet-to-be-developed object recognition algorithms may be used to extract the objects from the image data. Example object recognition algorithms include, but are not limited to, scale-invariant feature transform ("SIFT"), speeded up robust features ("SURF"), and edge-detection algorithms. The object recognition algorithm(s) may be embodied as software stored in the memory module 132, for example.

The objects extracted from the image data may be utilized by the processor 130 to generate a topographical map of the environment in which the visual-assist robot 100 is located. A topographical map is a map that provides spatial information regarding objects that are in the user's environment. For example, the topographical map may indicate the presence and position of particular objects, such as empty seats, doorways, tables, people, and the like. The topographical map may then be used to determine a navigational route for the visual-assist robot 100 to follow so that it may successfully arrive at the desired location indicated by the user.

Location data may also be utilized to develop a topographical map and resulting navigational route for the visual-assist robot 100 to follow. The physical location of the visual-assist robot 100 may be determined by any method. For example, the location sensor 150 may be used to determine the location of the visual-assist robot 100 (e.g., by a GPS sensor). Wireless signals, such as cellular signals, WiFi signals, and Bluetooth® signals may be used to determine the location of the visual-assist robot 100. Grid navigation may also be utilized. For example, the visual-assist robot 100 may communicate with an array of wireless signal emitters present within the environment to determine the location of the visual-assist robot 100.

The visual-assist robot 100 may also use topographical map information that is either stored in the memory module 132 or accessed from a remote location, such as a cellular telephone or a remote server. The topographical map information may include data relating to external maps, such as roads, footpaths, buildings, and the like. The topographical map information may also include data relating to interior spaces of buildings (e.g., location of rooms, doorways, walls, etc.). The topographical map information may provide additional information regarding the environment beyond the objects extracted from the image data. The processor 130 may access the topographical map information when generating the topographical map. The topographical map may comprise any combination of objects extracted from image data, the physical location of the visual-assist robot 100, and/or the topographical map information.

After the visual-assist robot 100 has navigated to the desired location, it may capture image data using the imaging assembly 122. It is noted that, in some cases, the user may place the visual-assist robot 100 in the desired location without it navigating to the desired location on its own. The user may instruct the visual-assist robot 100 to provide him with information regarding the environment. Accordingly, the visual-assist robot 100 will capture image data as described above and extract objects from the captured image data. In some embodiments, the visual-assist robot 100 may determine which particular objects in the environment are of interest to the user 202. Or, the user 202 may provide an input to the visual-assist robot as to which type of objects he wishes have more information about. As non-limiting examples, the user 202 may desire to know where the people are located in the environment, where there are empty tables, where there are empty seats, where there is a restaurant, where the exit is located, and where the restroom is located. Accordingly, the user 202 may instruct the visual-assist robot 100 to detect only a particular class or classes of objects within the environment.

The visual-assist robot 100 is configured to extract text that is present in the image data. For example, the visual-assist robot 100 may detect the text of signs 204A, 204B that are present within the environment. The processor 130, using a text-detection algorithm (e.g., optical character recognition), may detect and extract any text from the image data for inclusion in the message data provided to the user 202. As an example and not a limitation, the image data may have captured an "EXIT" sign in the environment. The processor 130 may detect and extract the word and location of the "EXIT" sign in the environment and, in the case of robot navigation, generate the topographical map accordingly. As described in more detail below, the message data provided to the user may indicate the presence and location of the "EXIT" sign to the user 202.

It is noted that any known or yet-to-be developed facial recognition algorithms may also be applied to the image data to detect particular people within the environment. For example, the user may input the names of particular people he or she would like to detect. Data regarding the facial features of people may be stored in the memory module 132 and accessed by the facial recognition algorithms when analyzing the image data. The message data may correspond to the names of people detected in the image data (e.g., "Both Tim and Steve are here.").

Returning to the use-case depicted in FIG. 6, the user 202 may instruct the visual-assist robot 100 to let him know what restaurants are in the vicinity. The processor 130 may extract relevant objects and text from the image data and provide the user 202 with message data corresponding to the requested information. The message data may be any form of non-visual communication. In one embodiment, the message data is communicated to the user as synthesized speech (i.e., audible message data) produced by the speaker 140. As an example, the visual-assist may produce synthesized speech that says: "There is a hamburger restaurant and a pizza restaurant to your left," or "there are four empty seats to your right" depending on the information requested by the user 202. For example, the processor 130 may have extracted objects and text (e.g., the text of signs 204A and 204B) to determine the presence and location of objects within the environment. The message data may also indicate an approximate number of steps to a particular restaurant or other desired object. The user 202 may ask the visual-assist robot 100 for additional, follow-up information, thereby having a dialog with the visual-assist robot 100.

Figure 7:
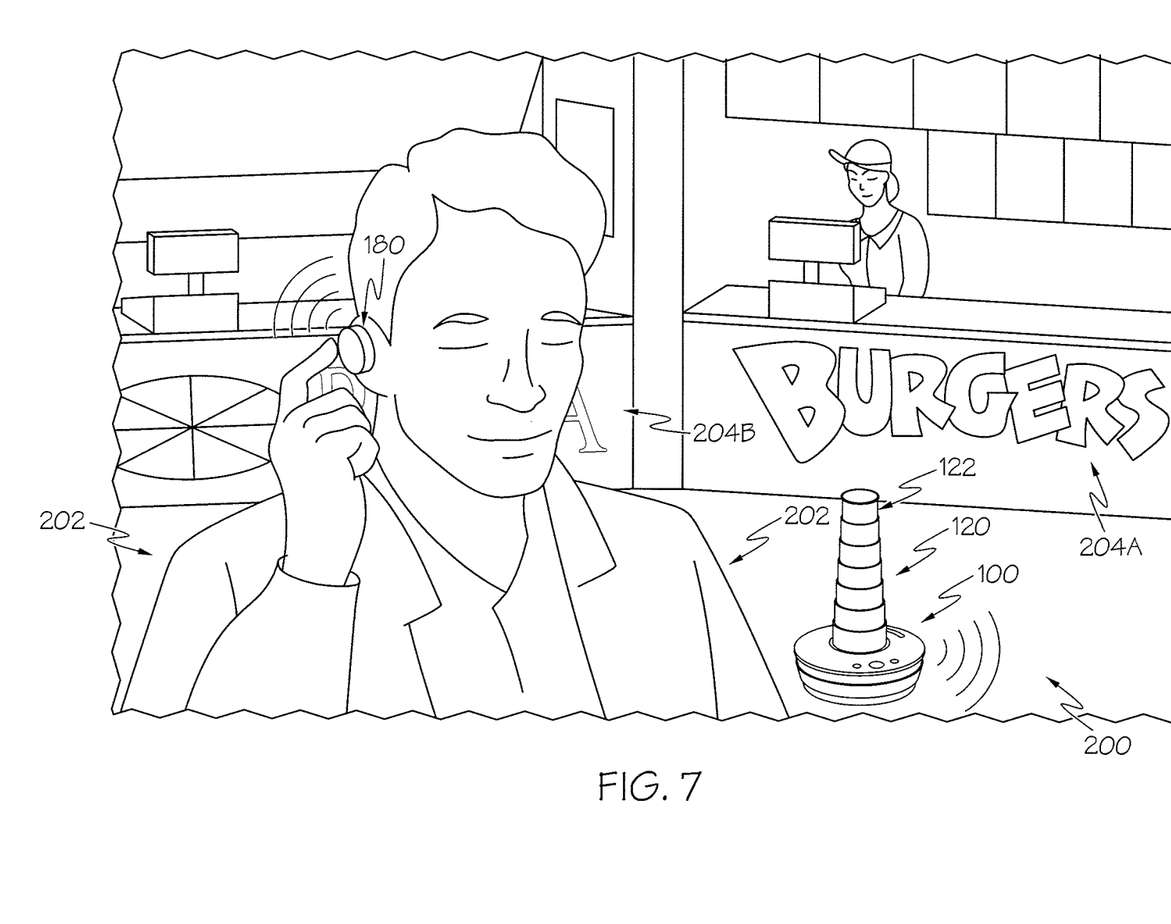

Referring now to FIG. 7, in some embodiments, the message data may be configured as a wireless signal that is communicated to a portable electronic device 180. In the illustrated embodiment, the portable electronic device 180 is an earpiece that is worn by the user 202. However, the portable electronic device 180 may be any type of electronic device, such as a cellular phone, portable digital assistance, a proprietary electronic device, and the like. The portable electronic device 180 may receive the message data configured as a wireless signal and then convert it to sound for receipt by the user. In some embodiments, the message data is configured as data for receipt and display by a tactile display device. For example, the portable electronic device 180 may be configured as a tactile display device that receives the wireless message data and converts it into a tactile message for display on the tactile display device. For example, Braille (or other tactile writing system) may be displayed and/or a tactile topographic map of the particular objects extracted from the image data.

Figure 8:
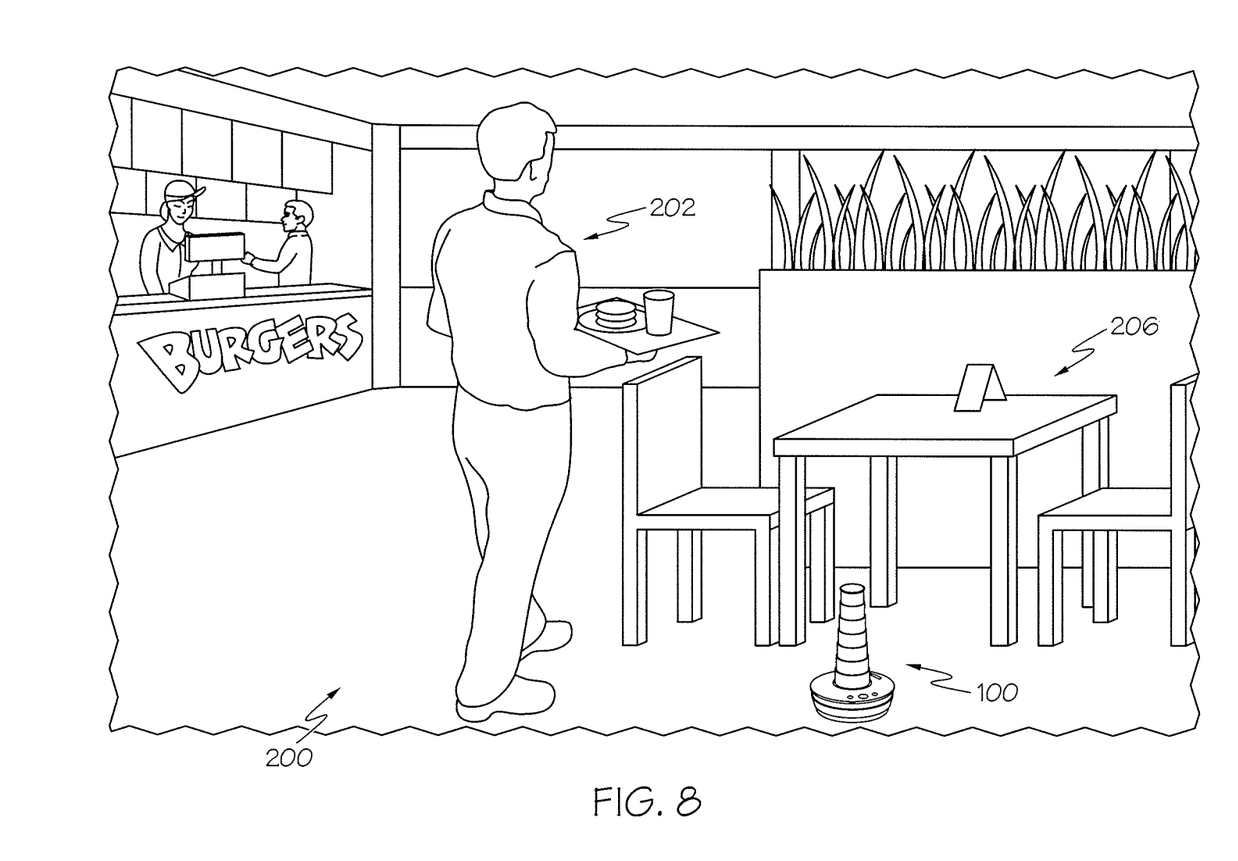

Referring now to FIG. 8, the user 202 has successfully ordered food from one of the restaurants and would now like to find an empty table and seat. Repeating the above-described process, the user 202 asks the visual-assist robot 100 to locate an empty table and seat. By analyzing the image data captured from the imaging assembly 122, the visual-assist robot 100 finds an empty table and seat 206. The visual-assist robot 100 may then provide the user 202 with message data indicating the location of the empty table and seat 206 within the environment. In some embodiments, the visual-assist robot 100 may lead the user 202 to the desired location, such as by emitting sounds that the user 202 may follow, or by leading the user 202 when the user is holding the retractable handle assembly 190.

It should now be understood that embodiments described herein are directed to small, portable visual-assist robots that may autonomously navigate to a desired location, capture image data, and, based on the image data, provide information to a user with respect to desired objects within the environment in a non-visual manner. The visual-assist robots described herein comprise an imaging assembly that may be raised above a base-portion of the robot, and may also be detachable from the robot.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A visual-assist robot comprising:
a housing defining a base portion, the base portion comprising an upper surface and a lower surface;
an imaging assembly, wherein the imaging assembly is configured to generate image data corresponding to an environment, and at least a portion of the imaging assembly is configured to be disposed above the upper surface of the base portion;
a motorized wheel assembly positioned at the lower surface of the base portion;
a processor disposed within the housing and communicatively coupled to the imaging assembly and the motorized wheel assembly; and
a non-transitory memory device disposed within the housing, the non-transitory memory device storing machine-readable instructions that, when executed by the processor, cause the processor to:
receive a user command to provide information about the environment;
provide a drive signal to the motorized wheel assembly such that the motorized wheel assembly moves the visual-assist robot to a desired location within the environment;
detect objects from image data received from the imaging assembly;
determine information from the image data relevant to the received user command about one or more objects of the objects detected, wherein the information relevant to the received user command includes a classification of each of the one or more objects; and
transmit message data for receipt by a user, wherein the message data provides an indication as to a presence of the one or more objects classified from the image data.

2. The visual-assist robot as claimed in claim 1, further comprising a speaker, wherein the message data is configured as an audio signal emitted by the speaker.

3. The visual-assist robot as claimed in claim 1, further comprising a wireless communication module configured to wirelessly communicate information with a portable electronic device, wherein the wireless communication module is communicatively coupled to the processor, and the machine-readable instructions further cause the processor to provide the message data to the wireless communication module for wireless transmission to the portable electronic device.

4. The visual-assist robot as claimed in claim 3, wherein the message data is configured as a wireless signal comprising an audio message for playback by a speaker of the portable electronic device.

5. The visual-assist robot as claimed in claim 1, wherein:
the drive signal is provided in accordance with the user command and controls the motorized wheel assembly such that the visual-assist robot autonomously navigates to the desired location within the environment; and
the machine-readable instructions further cause the processor to provide a second drive signal to the motorized wheel assembly such that the motorized wheel assembly moves the visual-assist robot to the user and leads the user to one of the one or more objects classified from the image data.

6. The visual-assist robot as claimed in claim 1, further comprising a location sensor communicatively coupled to the processor, wherein the location sensor is configured to provide location data to the processor based on a physical location of the visual-assist robot.

7. The visual-assist robot as claimed in claim 6, wherein the location sensor comprises a wireless signal sensor operable to wirelessly communicate with wireless signal emitters present within the environment.

8. The visual-assist robot as claimed in claim 1, wherein the non-transitory memory stores topographical map information, and the machine-readable instructions further cause the processor to:
access the topographical map information to retrieve topographical information corresponding to a location of the visual-assist robot within the environment; and
generate the message data based at least in part on the topographical information corresponding to the location of the visual-assist robot within the environment.

9. The visual-assist robot as claimed in claim 1, wherein the machine-readable instructions further cause the processor to extract text from the image data, and the message data provides information corresponding to the text extracted from the image data.

10. The visual-assist robot as claimed in claim 1, wherein the imaging assembly is configured such that the image data comprises one or more omni-directional images.

11. The visual-assist robot as claimed in claim 1, further comprising a retractable pedestal coupled to the imaging assembly, wherein:
when the retractable pedestal is in an extended position, the imaging assembly is disposed above the upper surface of the base portion; and
when the retractable pedestal is in a retracted position, the imaging assembly is at least partially disposed within the base portion.

12. The visual-assist robot as claimed in claim 11, wherein the imaging assembly comprises an imaging assembly housing that is removably coupled to the retractable pedestal.

13. The visual-assist robot as claimed in claim 11, wherein the imaging assembly comprises:
an imaging assembly housing;
an omni-directional mirror within the imaging assembly housing; and
a camera optically coupled to the omni-directional mirror.

14. The visual-assist robot as claimed in claim 13, wherein the camera is disposed within the base portion and the omni-directional mirror is disposed above the upper surface of the base portion when the retractable pedestal is in an extended position.

15. The visual-assist robot as claimed in claim 11, wherein the imaging assembly comprises an imaging assembly housing and an omni-directional camera within the imaging assembly housing.

16. The visual-assist robot as claimed in claim 1, further comprising a retractable handle assembly comprising a handle and a cord, wherein the upper surface of the base portion comprises a storage recess such that the handle and the cord are disposed within the storage recess when the retractable handle assembly is in a retracted position.

17. The visual-assist robot as claimed in claim 1, further comprising at least one carrying strap within the lower surface of the base portion, wherein the at least one carrying strap is configured to a disposed around a portion of the user when in an extended position, and the at least one carrying strap is at least partially disposed within the base portion when in a retracted position.

18. A visual-assist robot comprising:

a housing defining a base portion, the base portion comprising an upper surface and a lower surface;

an imaging assembly, wherein the imaging assembly is configured to generate image data corresponding to an environment, and at least a portion of the imaging assembly is configured to be disposed above the upper surface of the base portion;

a retractable pedestal comprising a plurality of segments configured to extend from the upper surface of the base portion, wherein the imaging assembly is coupled to the retractable pedestal such that:

when the retractable pedestal is in an extended position, the imaging assembly is disposed above the upper surface of the base portion; and when the retractable pedestal is in a retracted position, the plurality of segments is positioned in a nested arrangement and the imaging assembly is at least partially disposed within the base portion;

a motorized wheel assembly positioned at the lower surface of the base portion;

a wireless communication module configured to wirelessly communicate information with a portable electronic device;

a processor disposed within the housing and communicatively coupled to the imaging assembly, the motorized wheel assembly, and the wireless communication module; and a non-transitory memory device disposed within the housing, the non-transitory memory device storing machine-readable instructions that, when executed by the processor, cause the processor to:

provide a drive signal to the motorized wheel assembly to autonomously move the visual-assist robot to a desired location within the environment;

determine objects from the image data received from the imaging assembly; and provide message data to the wireless communication module for wireless transmission to the portable electronic device, wherein the message data provides an indication as to a presence of one or more objects determined from the image data.

19. The visual-assist robot as claimed in claim 18, wherein the machine-readable instructions further cause the processor to extract text from the image data, and the message data provides information corresponding to the text extracted from the image data.

20. The visual-assist robot as claimed in claim 18, wherein the imaging assembly comprises an imaging assembly housing that is removably coupled to the retractable pedestal.

* * * * *

UNITED STATES PATENT AND TRADEMARK OFFICE
CERTIFICATE OF CORRECTION

PATENT NO. : 9,530,058 B2
APPLICATION NO. : 14/567062
DATED : December 27, 2016
INVENTOR(S) : Douglas A. Moore et al.

Page 1 of 1

It is certified that error appears in the above-identified patent and that said Letters Patent is hereby corrected as shown below:

On the Title Page

In page 2, item (56), references cited, foreign patent documents, delete
"JP     20040033640 A     2/2004".

In page 2, item (56), references cited, other publications, delete
"Japan develops robot that could take the place of seeing-eye dogs for visually-impaired people, Fareastgizmos, (http://fareastgizmos.com/robotic/japan-develops-robot-take-place-seeing-- eye-dogs-visuallyirnpaired-people.php) (accessed Apr. 29, 2014)"
and insert
--Japan develops robot that could take the place of seeing-eye dogs for visually-impaired people, Fareastgizmos, (http://fareastgizmos.com/robotic/japan-develops-robot-take-place-seeing-- eye-dogs-visuallyimpaired-people.php) (accessed Apr. 29, 2014)--, therefor.

Signed and Sealed this
Twenty-eighth Day of March, 2017

Michelle K. Lee
*Director of the United States Patent and Trademark Office*